United States Patent
Cao

(10) Patent No.: US 8,101,204 B2
(45) Date of Patent: *Jan. 24, 2012

(54) HARD CAPSULE COMPOSITION AND METHOD OF USE

(76) Inventor: Karl Wei Cao, Richmond (CA)

( * ) Notice: Subject to any disclaimer, the term of this patent is extended or adjusted under 35 U.S.C. 154(b) by 227 days.

This patent is subject to a terminal disclaimer.

(21) Appl. No.: 12/687,295

(22) Filed: Jan. 14, 2010

(65) Prior Publication Data

US 2011/0171293 A1 Jul. 14, 2011

(51) Int. Cl.
*A61K 9/48* (2006.01)

(52) U.S. Cl. .................................. 424/451; 424/453

(58) Field of Classification Search .................. None
See application file for complete search history.

(56) References Cited

U.S. PATENT DOCUMENTS

| | | | |
|---|---|---|---|
| 6,214,376 B1 * | 4/2001 | Gennadios | 424/451 |
| 6,331,205 B1 | 12/2001 | Paris et al. | |
| 6,517,865 B2 | 2/2003 | Cade et al. | |
| 6,635,275 B1 | 10/2003 | Scott et al. | |
| 6,635,279 B2 | 10/2003 | Kolter et al. | |
| 6,783,770 B2 | 8/2004 | Angel et al. | |
| 6,887,307 B1 | 5/2005 | Scott et al. | |
| 6,949,256 B2 * | 9/2005 | Fonkwe et al. | 424/451 |
| 7,041,315 B2 | 5/2006 | Scott et al. | |
| 7,267,718 B2 | 9/2007 | Scott et al. | |
| 2001/0024678 A1 | 9/2001 | Scott et al. | |
| 2004/0091557 A1 | 5/2004 | Hamann | |
| 2006/0165775 A1 * | 7/2006 | Korshak et al. | 424/451 |

OTHER PUBLICATIONS

Nishi K; Osada T, Derwent 2005-377484.

* cited by examiner

*Primary Examiner* — Susan Tran

(74) *Attorney, Agent, or Firm* — Buskop Law Group, PC; Wendy Buskop

(57) ABSTRACT

A method for making clear hard vegetarian gelatin free two piece capsules by creating the first phase of the biphasic system using seaweed extract, gellan gum, metallic element, maltol extract, seaweed extract and water. A filler is created for the first phase of the biphasic network by blending water, galactomannan extract, and cellulose. The filler is then mixed into the system forming a biphasic system, a first pin is then dripped into the blend and then a second pin is then dripped into the blend. Blowing hot air on the dipped pins, which then blows away water on the outer surface of the dipped pins to bond and lock moisture to the cellulose. A large diameter capsule piece is removed from the first pin and a small diameter capsule piece is removed from the second pin, wherein each capsule piece has an outer surface which is mechanically and dimensionally stable.

20 Claims, No Drawings

HARD CAPSULE COMPOSITION AND METHOD OF USE

FIELD

The present embodiments generally relate to hard capsules produced in two pieces as empty capsules manufactured solely by using vegetable derivatives.

BACKGROUND

A need exists for a capsule that does not include gelatin or other substances elicited from animals due to the dangerous associate with gelatin and other substances elicited from animals. For example, the dangers associated with gelatin or other substances elicited from animals can include BSE (bovine spongiform encephalitis).

A further need exists for a capsule that is made from seven completely natural ingredients including water in a biphasic solution system that is maintained at a temperature of no more than 80 degrees Fahrenheit.

A need further exists for a capsule that is made from a moisture locking procedure that gives the vegetarian hard capsule a novel mechanical and dimensional stability, allowing the hard capsules the ability to be filled with extremely hygroscopic material, without crosslinking The present embodiments meet these needs.

DETAILED DESCRIPTION OF THE EMBODIMENTS

Before explaining the present invention in detail, it is to be understood that the invention is not limited to the particular embodiments and that it can be practiced or carried out in various ways.

The present embodiments relate to a biphasic system for manufacturing clear hard vegetarian gelatin free two piece capsules, using a conventional dipping method.

The disclosed compositions do not employ mammalian gelatin and, therefore, overcome the disadvantages associated with animal-derived material. Compositions of the invention do not contain any gelatin but, instead, require at least seven agents: 1) a cellulose and 2) a gum derivative and 3) a metallic element and 4) a maltol extract and 5) a seaweed extract and 6) a galactomannan extract and 7) a water.

One or more embodiments of the method can be used to make a clear hard vegetarian gelatin free two piece capsule.

The method can include making a first phase of the biphasic network system. Making the first phase can include using a seaweed extract, a maltol extract, a metallic element, a gum derivative and a water.

A second phase or filler can also be created by blending water, a galactomannan extract, and a cellulose ether at a temperature less than 80 Fahrenheit.

The filler can be mixed into the first phase network system forming a biphasic system or blend while maintaining a temperature of not more than 80 degrees Fahrenheit.

One or more first moulding pins or large diameter moulding pins can be dipped into the biphasic system or blend while maintaining the biphasic system or blend at a temperature of not more than 80 degrees Fahrenheit.

One or more second moulding pin or small diameter moulding pins can also be dipped into the blend or biphasic system while maintaining the blend or biphasic system at a temperature of not more then 80 degrees Fahrenheit.

The second moulding pin can have a diameter that is from about 1.0 percent to about 10.0 percent less than the diameter of the first moulding pin.

The dipped moulding pins can be put into a chamber with a humidity that is no more than about 25 percent and the water can be blown away from an outer surface of dipped moulding pins. The water can be blown away using blown hot air. The blown hot air can be at a temperature from about 70 degrees Celsius to about 77 degrees Celsius, thereby bonding or locking the water to the cellulose, rendering each capsule piece to have an outer surface resistant to humidity and moisture, while maintaining a brilliantly clear, mechanically and dimensionally stable hard capsule resistant to crosslinking and hygroscopic material. The clear hard vegetarian gelatin free two piece capsule surprisingly inhibits microbial activity by bonding or locking of the water to the cellulose of the clear hard vegetarian gelatin free two piece capsule upon drying.

The biphasic system produces a clear hard vegetarian gelatin free two piece capsule wherein a dosage amount can be inserted between the first and second capsule pieces. The first and second capsule pieces can be joined together with an interference fit forming a dosage capsule that resists cracking, brittleness, and some storage conditions, caused by the hot air blown onto the wet capsule, and bonding the moisture to the cellulose until a water activity measures from about 0.10 to about 0.60.

The cellulose of the biphasic system for the clear hard vegetarian gelatin free two piece capsule can be a methyl cellulose, hydroxyethyl cellulose, hydroxypropyl cellulose hydroxyethylmethyl cellulose, hydroxyethylethyl cellulose, hydroxypropylmethyl cellulose, cotton cellulose, or combinations thereof.

The seaweed extract for making a clear hard vegetarian gelatin free two piece capsule can be carrageenan, red seaweed, brown seaweed, funoran algae, red algae, brown algae, green algae, kelp, other marine plants, or combinations thereof.

The maltol extract can be crystalline and can be used for making a clear hard vegetarian gelatin free two piece capsule can be larch bark, pine needles, chicory and roasted malt, or combinations thereof.

The metallic element for making a clear hard vegetarian gelatin free two piece capsule can be potassium, magnesium, calcium, iron, or combinations thereof.

The gellan gum can be polysaccharides.

The galactomannan extract can be mannan, locust bean gum, carob, carob gum, carob bean gum, carboin, guar gum, tragacanth gum, or combinations thereof.

In one or more embodiments a crystalline alcohol can be added to the filler. The crystalline alcohol can be dextrose, glucose, sorbitol, manitol, fructose, fruit sugar derivative alcohols, or combinations thereof.

The clear hard vegetarian gelatin free two piece capsule can have gellan gum at a weight percent from about 0.5 to about 5.0, the seaweed exact at a weight percent from about 0.01 to about 5.0;, a metallic element at weight percent from about 0.01 to about 5.0, a maltol extract at weight percent from about 0.05 to about 12.0, the galatomannan extract at a weight percent from about 0.05 to about 5.0, the cellulose derivative at a weight percent from about 15.0 to about 45.0, and from about 60.0 to about 90.0 weight percent of water.

The clear hard vegetarian gelatin free two piece capsule can be a suppository or an oral dosage capsule.

The clear hard vegetarian gelatin free two piece capsule can have a dosage amount. The dosage amount can be a liquid or an oil, such as marine oil, a lipid, a vitamin, synthetic, a vegetable, or combinations thereof.

In one or more embodiments, the dosage amount can be a dry botanical ingredient, botanical, marine extract, a vitamin supplement, or combinations thereof.

The dosage amount can be a dry or liquid pharmaceutical dosage amount that can be aspirin, antihistamine, acetaminophen, an anti-inflammatory, or an antibiotic, or combinations thereof.

The dosage amount can be a nutritional dosage amount.

The clear hard vegetarian gelatin free two piece capsule can also contain a flavoring additive added to the filler, the first phase network, or combinations thereof. The flavorings can include citrus flavoring, mint flavoring, rum flavoring, fruit flavoring, bubblegum flavoring, vanilla flavoring, chocolate flavoring, licorice flavoring, coffee flavoring, or combinations thereof.

The clear hard vegetarian gelatin free two piece capsule can also have an edible coloring added to the first phase network, the filler or combinations thereof. The edible coloring can be azoquinophthalone triphenylmethane, xanthene, indigoid dyes, iron oxides, iron hydroxides, titanium dioxides, carbon black, riboflavin, carotenes, anthocyanines, tumeric, cochineal extracts, chlorophyllin, canthaxanthin, caramel, betannin, or combinations thereof.

The clear hard vegetarian gelatin free two piece capsule can also have a coating or banding. The coating or banding can be a polysaccharide or a second cellulose.

While these embodiments have been described with emphasis on the embodiments, it should be understood that within the scope of the appended claims, the embodiments might be practiced other than as specifically described herein.

What is claimed is:

1. A method for making a clear hard vegetarian gelatin free two piece capsule consisting essentially of:
   a. creating a first phase of a biphasic system using a seaweed extract, a gellan gum, a metallic element, a maltol extract, and water;
   b. creating a filler for the first phase of the biphasic network by blending water, a crystalline alcohol, a galactomannan extract, and a cellulose at a temperature less than 80 Fahrenheit;
   c. mixing the filler into the first phase network system forming a biphasic system;
   d. dipping a first pin with a large diameter into the blend while maintaining the blend a temperature of not more than 80 degrees Fahrenheit;
   e. dipping a second pin with a small diameter into the blend while maintaining the blend at a temperature of not more than 80 degrees Fahrenheit and wherein the second pin small diameter is from 1 percent to 10 percent less in diameter than the large diameter;
   f. blowing hot air on the dipped pins in a chamber with a humidity that is no more than 25 percent blowing away water on an outer surface of the dipped pins to bond and lock moisture to the cellulose, the remaining moisture level is from 5.0 to 7.0 percent;
   g. removing a large diameter capsule piece from the first pin and a small diameter capsule piece from the second pin, wherein each capsule piece has an outer surface which is mechanically and dimensionally stable; and
   h. inserting a dosage amount between the first and second capsule pieces, assembling the capsule pieces together with an interference fit forming a dosage capsule that resists cracking, brittleness, and humidity and moisture conditions.

2. The method for making a clear hard vegetarian gelatin free two piece capsule of claim 1, wherein the dosage amount is dry or liquid.

3. The method for making a clear hard vegetarian gelatin free two piece capsule of claim 2, wherein the liquid is a liquid extract, a liquid oil, a marine oil, a fish oil, a lipid, an oil vitamin, a synthetic oil, a vegetable oil, or combinations thereof.

4. The method for making a clear hard vegetarian gelatin free two piece capsule of claim 1, wherein the dosage amount is a member of the group consisting of:
   a dry botanical ingredient, a marine extract, a vitamin supplement, or combinations thereof.

5. The method for making a clear hard vegetarian gelatin free two piece capsule of claim 1, wherein the dosage amount is a pharmaceutical dosage amount.

6. The method for making a clear hard vegetarian gelatin free two piece capsule of claim 5, wherein the pharmaceutical dosage amount that is a member of the group consisting of:
   aspirin, antihistamine, acetaminophen, an anti-inflammatory, an antibiotic, and combinations thereof.

7. The method for making a clear hard vegetarian gelatin free two piece capsule of claim 1, wherein the dosage amount is a nutritional dosage amount.

8. The method for making a clear hard vegetarian gelatin free two piece capsule of claim 1, wherein the hot air is at a temperature from 70 degrees Celsius to 77 degrees Celsius.

9. The method for making a clear hard vegetarian gelatin free two piece capsule of claim 1, wherein the hot air is blown on the capsule until a water activity measures from 0.10 to 0.60.

10. The method for making a clear hard vegetarian gelatin free two piece capsule of claim 1, wherein the maltol extract is a member of the group consisting of:
    larch bark, pine needles, chicory and roasted malt, and combinations thereof.

11. The method for making a clear hard vegetarian gelatin free two piece capsule of claim 1, wherein the seaweed extract is a member of the group consisting of:
    carrageenan, red seaweed, brown seaweed, funoran algae, red algae, brown algae, green algae, kelp, other marine plants, and combinations thereof.

12. The method for making a clear hard vegetarian gelatin free two piece capsule of claim 1, wherein the metallic element is a member of the group consisting of:
    potassium, magnesium, calcium, iron and combinations thereof.

13. The method for making a clear hard vegetarian gelatin free two piece capsule of claim 1, wherein the gellan gum is a member of the group consisting of:
    polysaccharides and combinations thereof.

14. The method for making a clear hard vegetarian gelatin free two piece capsule of claim 1, wherein the crystalline alcohol is a member of the group consisting of:
    dextrose, glucose, sorbitol, manitol, fructose, fruit sugar derivative alcohols, and combinations thereof.

15. The method for making a clear hard vegetarian gelatin free two piece capsule of claim 1, wherein the galactomannan extract is a member of the group consisting of:
    mannan, locust bean gum, carob, carob gum, carob bean gum, carboin, guar gum, tragacanth gum, and combinations thereof.

16. The method for making a clear hard vegetarian gelatin free two piece capsule of claim 1, wherein the clear hard vegetarian gelatin free two piece capsule is a suppository or an oral dosage capsule.

17. The method for making a clear hard vegetarian gelatin free two piece capsule of claim 1, further comprises the step of adding a flavoring additive to the filler, the first phase network or combinations thereof.

18. The method for making a clear hard vegetarian gelatin free two piece capsule of claim 16, wherein the flavoring additive is a member of the group consisting of:

citrus flavoring, mint flavoring, rum flavors, other fruit flavors, bubblegum flavoring, vanilla flavoring, chocolate flavoring, licorice flavoring or coffee flavoring, and combinations thereof.

19. The method for making a clear hard vegetarian gelatin free two piece capsule of claim 1, further comprising the step of adding an edible coloring to the first phase network, the filler or combinations thereof.

20. The method for making a clear hard vegetarian gelatin free two piece capsule of claim 18, wherein the edible coloring is a member of the group consisting of:

azoquinophthalone triphenylmethane, xanthene, or indigoid dyes, iron oxides, iron hydroxides, titanium dioxides, carbon black, riboflavin, carotenes, anthocyanines, tumeric, cochineal extracts, chlorophyllin, canthaxanthin, caramel, betannin, and combinations thereof.

* * * * *